United States Patent
Amey et al.

(10) Patent No.: US 6,245,350 B1
(45) Date of Patent: *Jun. 12, 2001

(54) PROCESS FOR ENCAPSULATION OF CAPLETS IN A CAPSULE AND SOLID DOSAGE FORMS OBTAINABLE BY SUCH PROCESS

(75) Inventors: James Amey, Greenwood, SC (US); Dominique Cade, Colmar (FR); Paul Maes, Mortsel; Robert Scott, Waasmunster, both of (BE)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/628,823

(22) Filed: Apr. 5, 1996

Related U.S. Application Data

(63) Continuation-in-part of application No. 08/585,549, filed on Jan. 11, 1996, now Pat. No. 6,080,426, which is a continuation of application No. 08/358,137, filed on Dec. 16, 1994, now abandoned.

(51) Int. Cl.[7] ........................................ A61K 9/48
(52) U.S. Cl. ............... 424/456; 424/451; 424/452; 424/453; 424/454; 424/463; 514/772.3; 514/773; 514/770; 514/774; 514/775; 514/778; 514/779; 514/781; 514/782; 514/783; 514/784
(58) Field of Search ..................... 424/451, 452, 424/453, 454, 456, 463, 457

(56) References Cited

U.S. PATENT DOCUMENTS

| | | |
|---|---|---|
| 599,865 | 3/1898 | Richards . |
| 724,436 | 4/1903 | Clark . |
| 1,520,940 | 12/1924 | Dulitz . |
| 1,657,982 | 1/1928 | Wilkie et al. . |
| 1,685,392 | 9/1928 | Beadle . |
| 1,774,258 | 8/1930 | English . |
| 1,872,190 | 8/1932 | Sindl . |
| 1,931,765 | 10/1933 | Leever .......................... 53/3 |
| 2,663,130 | 12/1953 | Donofrio ................. 53/89.5 |
| 3,045,641 | 7/1962 | Oddo . |
| 3,185,626 | 5/1965 | Baker ....................... 167/82 |
| 3,228,789 | 1/1966 | Glassman .............. 117/118 |
| 3,258,115 | 6/1966 | Kath . |
| 3,886,940 | 6/1975 | Hunger . |
| 3,896,762 | 7/1975 | Baker ........................ 118/30 |
| 3,983,258 | 9/1976 | Weaver ................... 426/307 |
| 4,562,024 | 12/1985 | Rogerson ................ 264/117 |
| 4,591,500 | 5/1986 | Scapinelli . |
| 4,684,516 | 8/1987 | Bhutani ..................... 424/19 |
| 4,793,119 | 12/1988 | Maso ..................... 53/139.3 |
| 4,820,524 | 4/1989 | Berta . |
| 4,844,906 | 7/1989 | Hermelin et al. . |
| 4,851,230 | 7/1989 | Tencza . |
| 4,867,983 | 9/1989 | Berta . |
| 4,921,108 | 5/1990 | Berta . |
| 4,928,840 | 5/1990 | Barshay et al. . |
| 4,936,074 | 6/1990 | Graham ...................... 53/440 |
| 4,965,089 | 10/1990 | Sauter et al. . |
| 4,966,771 | 10/1990 | Berta . |
| 4,973,480 | 11/1990 | Hermelin et al. . |
| 4,990,358 | 2/1991 | Berta . |
| 5,074,426 | 12/1991 | Goodhart et al. ......... 220/4.24 |
| 5,081,822 | 1/1992 | Boyd et al. ................ 53/468 |
| 5,085,033 | 2/1992 | Graham ...................... 53/436 |
| 5,089,270 | 2/1992 | Hampton et al. . |
| 5,098,715 | 3/1992 | McCabe et al. . |
| 5,114,720 | 5/1992 | Littell et al. . |
| 5,146,730 | 9/1992 | Sadek et al. . |
| 5,188,688 | 2/1993 | Boardman et al. ......... 156/69 |
| 5,198,227 | 3/1993 | Batista et al. . |
| 5,213,738 | 5/1993 | Hampton et al. .......... 264/113 |
| 5,415,868 | 5/1995 | Smith et al. .............. 424/454 |
| 5,456,919 | * 10/1995 | Patell et al. .............. 424/451 |
| 5,460,824 | * 10/1995 | Le Brun et al. ........... 424/453 |
| 6,080,426 | * 6/2000 | Amey et al. .............. 424/456 |

FOREIGN PATENT DOCUMENTS

| | | |
|---|---|---|
| 2428397 | 9/1977 | (DE) . |
| 0225565 | 6/1987 | (EP) . |
| 0435726 | 7/1991 | (EP) . |
| 9403365 | 2/1994 | (EP) . |
| 9618370 | 6/1996 | (EP) . |
| 1421144 | 1/1976 | (GB) . |
| 2149377 | 6/1985 | (GB) . |

OTHER PUBLICATIONS

Tablet Coating, Ellis, John R., et al.—pp. 197–225 & 380, 1951 1–1838.
Coating of Pharmaceutical Dosage Forms, Robinson, M.J.—pp. 1608–1617 1–1902.

* cited by examiner

*Primary Examiner*—James M. Spear
(74) *Attorney, Agent, or Firm*—Evan J. Federman

(57) ABSTRACT

A process for encapsulation of caplets in a capsule comprises the following steps: a. providing empty capsule parts; b. filling at least one of said capsule parts with one or more caplets; c. putting said capsule parts together; and d. treating the combined parts by cold shrinking. The solid dosage forms obtainable by such a process are tamper-proof in that they cannot be opened in a way to be reassembled without showing such opening process.

50 Claims, No Drawings

PROCESS FOR ENCAPSULATION OF CAPLETS IN A CAPSULE AND SOLID DOSAGE FORMS OBTAINABLE BY SUCH PROCESS

This is a continuation-in-part of application Ser. No. 08/585,549 U.S. Pat. No. 6,080,426 filed on Jan. 11, 1996, which is a continuation of Ser. No. 08/358,137 filed on Dec. 16, 1994 and now abandoned.

FIELD OF THE INVENTION

The present invention relates to a process for encapsulation of caplets in a capsule and to solid dosage forms obtainable by such a process, and more particularly, to the manufacture of a tamper-proof capsule containing a pharmaceutically active composition.

BACKGROUND OF THE INVENTION

Various oral medications have been manufactured in the form of so called caplets, which can be swallowed by patients during their regiment of taking medication. Caplets, however, are not as easily swallowed by patients as capsules having, for example, a gelatin coating. Additionally, capsule coatings are desirable over caplets since the coatings provide a neutral taste in contrast to caplets per se which sometimes contain pharmaceutical substances that taste, for example, bitter. Thus, patients, in particular children, refuse to swallow such caplets per se. Attempts have therefore been made to encapsulate caplets in a capsule by means of a gelatin cover.

U.S. Pat. No. 4,867,983 to Berta describes a method for double dipping gelatin coated caplets. The method provides a procedure for coating solid cores, such as caplets, with a first gelatinous coating on one end, and then with a second gelatinous coating on the other end which is thicker than the first, to simulate the interlocking halves of a hollow capsule. The second, thicker gelatinous coating can be provided with a single gelatin coating from a bath having a higher viscosity than the bath used to provide the first gelatinous coating. Alternatively, the second gelatinous coating can be provided by double dipping to provide layers of gelatinous material of gelatin. This known coating is disadvantageous in that the gelatinous coating and the color distribution is not uniformly distributed over the caplets by this process. Moreover, an overlapping of the different coatings results in color changes of the coatings. Additionally, the dip margins obtained by the known process tend not to be straight. Furthermore, the coatings according to the above patent chip off under stress if the coated caplets are stored under dry conditions and/or high temperature. Finally, the dip coating process of U.S. Pat. No. 4,867,983 is timed consuming and expensive.

From U.S. Pat. No. 5,081,822 to Boyd et al, an automatic caplet filler is known for filling normal gelatin capsules with caplets. The capsules formed by this automatic caplet filler, however, are disadvantageous in that they can be easily manipulated. Sealing of the capsules has to be effected by means of an additional gelatin strip or by gluing of the caplets in the capsule with an adhesive, as e.g. described in U.S. Pat. No. 4,928,840 or European Patent Application No. 0435726. This further treatment of the capsules may have the effect that substances other than the medication are encapsulated in the capsule. If on one hand a water-based adhesive is used for gluing the capsule halves together, the capsule as well as the caplet may be deformed. If on the other hand, an adhesive containing an organic solvent is used, a brittleness of the capsule will be the result. Finally, if the capsule halves are connected with each other by means of a heat shrinking process, a visible gap will remain between the capsule halves.

It is therefore the object of the present invention to provide a method for encapsulating caplets in a capsule in a tamper-proof form. It is yet another object of the invention to provide a cost-effective process for easily manufacturing tamper-proof solid dosage forms. It is yet another object of the present invention to provide a solid dosage form comprising a caplet covered by a capsule. It is yet another object of the present invention to provide a pharmaceutical dosage form having a greater resistance to breaking than known products. A further object of the present invention is to provide a tamper-proof solid dosage form.

SUMMARY OF THE INVENTION

According to a first aspect, the present invention provides a process for encapsulation of a caplet in a capsule by cold shrinking together capsule parts, which are filled with a caplet. According to another aspect, the present invention provides a solid dosage form obtainable by such a process. The solid dosage form according to the present invention is tamper-proof in that the caplet contained in the capsule cannot be removed from the capsule without destroying same.

The process according to the present invention furthermore provides a capsule product comprising several parts, which are combined with each other in a way that no visible slits between the capsule parts are present after the cold shrink procedure. The solid dosage forms of the present invention have a completely smooth surface, so that same can be swallowed easily by patients. More specifically, a process for encapsulating caplets in a capsule is provided, which comprises the following steps:

a. providing empty capsule parts,
b. filling at least one of said capsule parts with one or more caplets,
c. putting said capsule parts together, and
d. treating the combined capsule parts by cold shrinking.

Moreover, a solid dosage form comprising a caplet and capsule coating obtainable by such process is described.

DESCRIPTION OF PREFERRED EMBODIMENTS OF THE INVENTION

The capsule shell in which the caplet is to be enclosed preferably comprises two shell halves, a body portion and a cap portion. Other capsules comprising more than two parts are also possible. The capsule is typically a hollow shell of generally cylindrical shape having a diameter and length sufficient so that the caplet fits appropriately in the empty capsule. The clearance of the capsule shell and the caplet is preferably about +0.5 mm. According to a specifically preferred embodiment of the present invention, the clearance of the capsule shell and the caplet is in the range of from about 0 to about −0.5 mm, which means that the caplet is compressed in the capsule.

A specifically preferred process of the present invention is carried out as follows. Empty capsule parts are either kept after production at humid conditions in the range of from about 40 to about 90%, particularly from about 60 to about 80%, relative humidity to retain a moisture content of from about 14 to about 19% by weight of the capsule shell, preferably from about 15 to about 18% and more preferably from about 16 to about 18%, or are re-humidified to said moisture content before feeding into a capsule filling machine.

The first capsule shell part is then kept under humid conditions within the filling machine at said moisture content during rectifying and assembling with a caplet having a moisture content in the range of from about 0 to about 12% by weight.

A second or further capsule shell part is process in the same matter as the first one. Finally, the encapsulated dosage form is dried at a relative humidity in the range of from about 20 to about 40% and a temperature in the range of from about 15 to about 60 C, preferably from about 15 to about 40 C, more preferably from about 18 to about 25 C.

Caplets having a low moisture content of in the range of from about 0 to about 6% by weight, or more preferably of from about 0 to about 3% by weight, are especially suitable to be used in the process of the present invention. Conical ends of the caplet make the insertion of the caplet into one half of the capsule easier. After drying and shrinking the capsule parts together, the capsule can be further film coated, which coating may be enteric.

The capsule shell material can be a hydrophilic polymer, gelatin being the preferred choice. Other suitable capsule shell materials include starch, casein, chitosan, soya bean protein, safflower protein, alginates, gellan gum, carrageenan, xanthan gum, phtalated gelatin, succinated gelatin, cellulosephtalate-acetate, polyvinylacetate, hydroxypropyl methylcellulose, polyvinylacetate-phthalate, polymerisates of acrylic or methacrylic esters or mixtures thereof. The capsule shell material may furthermore contain from about 0 to about 40% pharmaceutically acceptable plasticizers based upon the weight of the hydrophilic polymer. The plasticizers which may be employed can be selected from polyethylene glycol, glycerol, sorbitol, dioctyl-sodium sulfosuccinate, triethyl citrate, tributyl citrate, 1,2-propyleneglycol, mono-, di, or tri-acetates of glycerol or mixtures thereof.

Additionally, the capsule shell material may contain pharmaceutically acceptable lubricants in the range of from about 0 to about 10% based upon the weight of the hydrophilic polymer. The lubricant may be selected from aluminumstearate, calciumstearate, magnesiumstearate, tinstearate talc, sodium lauryl sulfate, lecithins, mineral oils, stearic acid or silicones or mixtures thereof.

Moreover, the capsule shell material may contain pharmaceutically acceptable coloring agents in the range of from about 0 to about 10% based upon the weight of the hydrophilic polymer. The coloring agent may be selected from azo-quinophthalone-, triphenylmethane-, xanthene-dyes, iron oxides or hydroxides, titanium dioxide or natural dyes or mixtures thereof. Further suitable coloring agents are sunset yellow, allura red, amaranth, cochineal red, azogeranine, tartrazine, brilliant black, canthaxanthin, patent blue, fast green, brilliant blue, acid green, erythrosine, quinoline yellow, indigotine, curcumin or carbon black.

Furthermore, the capsule shell material may contain pharmaceutically acceptable extenders in the range of from about 0 to about 95% based upon the weight of the hydrophilic polymer. The extender may be selected from sunflower proteins, soybean proteins, cotton seed proteins, peanut proteins, rape seed proteins, lactose, gum arabic, acrylates or methacrylates, cellulose acetyl phthalates, hydroxypropyl cellulose, hydroxypropyl methylcellulose, hydroxypropyl methylcellulosephthalate, hydroxymethylcellulose, polyvinylpyrrolidone, shellac, bentonite, polyvinylacetatephthalate, phthalated gelatin, succinated gelatin, agar agar, hydroxyalkylstarches or mixtures thereof.

The solid pharmaceutical dosage form according to the present invention also may comprise a coating selected from cellacephate, polyvinyl acetate phthalate, methacrylic acid polymers, hypromellose phthalate, hydroxyalkyl methy cellulose phthalates or mixtures thereof.

The capsule parts of the solid dosage form of the present invention may have the same or different lengths and/or the same or different color. In the contact area of the capsule parts, the solid dosage form may be banded or easily dividable. The caplet being contained in the capsule can have a preformed step or groove in the dividing position of the capsule. To furthermore improve the caplet which is contained in the capsule, the caplet can be coated with an acceptable coating for tablet processing. In some cases, uncoated caplets are, however, preferred. A better contact between the inner shells of the capsule parts and the caplets can be obtained by treating the inner shells and/or the surface of the caplet with an adhesive. A suitable technique to apply the adhesive is spraying same on the shells and caplets immediately before assembling same. Suitable adhesives are e.g. tackidex or an aqueous gelatin solution.

A further aspect of the present invention is to provide encapsulated dosage forms in which the capsule shell halves do not completely cover the entire caplet, which means the caplet is longer than the combined length of the shell halves. This will provide capsules with additional advantageous features. For example, if each of the capsule halves has a different color and the caplet has a third color, a three-colored capsule will be obtained, or, if the shell halves have the same color and the caplet has a different color, a color banded capsule will be obtained. A second optional feature may be obtained by use of enteric coated capsule shell halves. In such a case a capsule with delayed release will be obtained, releasing the medicament in the stomach first from the small release band between the shell halves and later from the capsule openings.

A further aspect of the invention is the use of the described moisture control and rehumidification on common encapsulation machines with all kinds of common hard gelatin capsule types. The inventive process gives much better filling results especially with filling machines in hot and dry areas for the encapsulation of all kinds of fillings such as powders, pellets, liquids, microcapsules, tablets, etc. The preferred process in this case is carried out as follows: Empty capsule bodies and the preferred capsules are assembled in a pre-lock state and are either kept after production at humid conditions of 40 to 90% humidity, preferably 60 to 80% relative humidity to retain a moisture content of about 14 to about 19%, preferably about 15 to about 18% and most preferably about 16% to about 18% by weight of the capsule shell or are rehumidified to said moisture before opening and sorting in the capsule filling machine. Capsule bodies are then kept under humid conditions within the filling machine at said moisture content during rectifying and filling with the desired product. In the same way, the capsule caps are kept at moisture content during the rectifying and finally assembling with the filled capsule bodies. Finally, the capsule is dried at 20 to 40% relative humidity and a temperature of about 15 to about 60 C, preferably about 15 to about 40 C and most preferably at about 18 to about 25 C.

The solid dosage form according to the present invention may, for example, comprise a pharmaceutically or agrochemically active composition. Furthermore comprised in the solid dosage form can, for example, be a foodstuff or a dyestuff composition. In case the solid dosage form of the present invention contains a pharmaceutical composition, the active substance of same can, for example, be selected from betamethasone, thioctic acid, sotalol, salbutamol, norfenefrine, silymarin, dihydroergotamine, buflomedil, etofibrate, indomethacin, oxazepam, acetyldigitoxins, piroxicam, haloperidol, isosorbide mononitrate, amitriptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovirmononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydrogenmaleate, bezafibrate, isosorbide dinitrate, gallopamil, xantinolnicotinate, digitoxin, flunitrazepam, bencyclane, depanthenol, pindolol, lorazepam, diltiazem, piracetam, phenoxymethylpenicillin, furosemide, bromazepam, flunarizine, erythromycin, metoclopramide, acemetacin, ranitidine, biperiden, metamizol, doxepin, dipotassiumchlorazepat, tetrazepam, estramustinephosphate, terbutaline, captopril, maprotiline, prazosin, atenolol, glibenclamid, cefaclor, etilefrin, cimetidine, theophylline, hydromorphone, ibuprofen, primidone, clobazam, oxaceprol, medroxyprogesterone, flecainide, Mg-pyridoxal-5-phosphateglutaminate, hymechromone, etofyllineclofibrate, vincamine, cinnarizine, diazepam, ketoprofen, flupentixol, molsidomine, glibornuride, dimethindene, melperone, soquinolol, dihydrocodeine, clomethiazole, clemastine, glisoxepid, kallidinogenase, oxyfedrine, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, mebeverine, bisacodyl, 5-amino-salicyclic acid, dihydralazine, magaldrate, phenprocoumon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, B-carotene, cloramphenicol, chlorodiazepoxid, chlormadinoneacetate, chlorothiazide, cinnarizine, clonazepam, codeine, dexamethasone, dicumarol, digoxin, drotaverine, gramicidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbital, phenylbutazone, phenytoin, prednisone, reserpine, spironolactine, streptomycin, sulfamethizole, sulfamethazine, sulfamethoxazole, sulfamethoxydiazinon, sulfathiazole, sulfisoxazole, testosterone, tolazamide, tolbutamide, trimethoprim, tyrothricin or mixtures thereof.

The purpose of the above description is to illustrate various configurations and uses of the present invention, without implying any limitation. It will be apparent to those skilled in the art that various modifications and variations may be made in the process and product of the invention without departing from the spirit or scope of the invention.

We claim:

1. A process for the encapsulation of caplets in a capsule, comprising the following steps:
   a. providing empty first and second capsule shell parts,
   b. filling at least one of said capsule parts with one or more caplets, wherein the clearance between the capsule part and the caplet is in the range of from $-0.5$–$0.5$ mm.,
   c. putting said capsule parts together,
   d. treating the combined capsule parts by cold shrinking, wherein the empty capsule parts are either kept after production at humid conditions in the range of from about 40 to about 90% relative humidity to retain a moisture content in the range of from about 14 to about 19% by weight of the capsule shell or are re-humidified to said moisture content before feeding into a capsule filling machine and wherein the first capsule part is kept under humid conditions within the filling machine at said moisture content during rectifying and assembling with a caplet having a moisture content in the range of from about 0 to about 12% by weight the second capsule part is processed in the same manner, and the encapsulated dosage form is dried at a relative humidity in the range of from about 20 to about 40% and a temperature in the range of from about 15 to about 60 C.

2. The process according to claim 1 wherein the caplets comprise a compressed material.

3. The process according to claim 1 wherein the moisture content is in the range of from about 15 to about 18% by weight of the capsule shell by weight.

4. The process according to claim 3, wherein the moisture content is in the range of from about 16 to about 18% by weight.

5. The process according to claim 1, wherein the encapsulated dosage form is dried at a temperature in the range of from about 15 to about 40 C.

6. The process according to claim 5, wherein the encapsulated dosage form is dried at a temperature in the range of from about 18 to about 25 C.

7. The process according to claim 1, wherein the capsule parts are maintained at a relative humidity in the range of from about 60 to about 80% during the steps of feeding into a capsule filling machine, rectifying and assembling.

8. The process according to claim 7, wherein the moisture content of the capsule parts is in the range of from about 16 to about 18% by weight.

9. The process according to claim 1 wherein the moisture content of the caplet is in the range of from about 0 to about 6% by weight.

10. The process according to claim 1, wherein the moisture content of the caplet is in the range of from about 0 to about 3% by weight.

11. The process according to claim 1, wherein the caplet has conical ends.

12. A process for filling hard gelatin capsule comprising:
    maintaining empty capsule bodies and caps or pre-assembled capsule bodies after production at humid conditions of about 40 to about 90% relative humidity to retain a moisture content of about 14 to about 19% by weight of the capsule shell or are re-humidified to said moisture content before feeding into a capsule filling machine;
    maintaining the capsule body under humid conditions within the filling machine at said moisture content during rectifying and filling; and
    maintaining the capsule cap under the same conditions until assembled with the body, and the encapsulated dosage form is dried at about 20 to about 40% relative humidity and a temperature of about 15 to about 60 C.

13. The process according to claim 12 wherein the moisture content is about 15 to about 18% by weight of the capsule shell.

14. The process according to claim 1, wherein after drying and shrinking of the capsule parts the encapsulated dosage form is film-coated.

15. Process according to claim 14, wherein the coating is enteric.

16. A solid dosage form obtainable according to the process of claim 1.

17. A solid dosage form according to claim 7, wherein the capsule part material comprises a hydrophilic polymer.

18. A solid dosage form according to claim 7, wherein the capsule part material is selected from the group consisting of gelatin, starch casein, chitosan, soya bean protein, safflower protein, alginates, gellan gum, carrageenan, xanthan gum, phthalated gelatin, succinated gelatin, cellulosephtalate-acetate, polyvinylacetate, hydroxypropyl methylcellulose, polycinylacetate-phthalate, polymerisates of acrylic or methacrylic esters and mixtures thereof.

19. A solid dosage form according to claim 17, wherein the capsule part material contains pharmaceutically acceptable plasticizers in the range of from about 0 to about 40% based upon the weight of the hydrophilic polymer.

20. A solid dosage form according to claim 19, wherein the plasticizer is selected from the group consisting of polyethylene glycol, glycerol, sorbitol, dioctyl-sodium sulfosuccinate, triethyl citrate, tributyl citrate, 1,2-propyleneglycol, mono-, di- or tri-acetates of glycerol and mixtures thereof.

21. A solid dosage form according to claim 17, wherein the capsule part material contains pharmaceutically acceptable lubricants in the range of from about 0 to about 10% based upon the weight of the hydrophilic polymer.

22. A solid dosage form according to claim 21, wherein the lubricant is selected from the group consisting of aluminumstearate, calciumstearate, magnesiumstearate, tinstearate, talc, sodium lauryl sulfate, lecithins, mineral oils, stearic acid or silicones and mixtures thereof.

23. A solid dosage form according to claim 17, wherein the capsule part material contains pharmaceutically acceptable coloring agents in the range of from about 0 to about 10% based upon the weight of the hydrophilic polymer.

24. A solid dosage form according to claim 23, wherein the coloring agent is selected from the group consisting of azoquinophthalone-, triphenylmethane-, xanthene-dyes, iron oxides or hydroxides, titanium dioxide or natural dyes and mixtures thereof.

25. A solid dosage form according to claim 23, wherein the coloring agent is selected from sunset yellow, allura red, amaranth, cochineal red, azogeranine, tartrazine, brilliant black, canthaxanthin, patent blue, fast green, brilliant blue, acid green, erythrosine, quinoline yellow, indigotine, curcumin or carbon black.

26. A solid dosage form according to claim 17, wherein the capsule part material contains pharmaceutically acceptable extenders in the range of from about 0 to about 95% based upon the weight of the hydrophilic polymer.

27. A solid dosage form according to claim 4, wherein the capsule part material contains an extender.

28. A solid dosage form according to claim 27, wherein the extender is selected from the group consisting of sunflower proteins, soy bean proteins, cotton seed proteins, peanut proteins, rape seed proteins, lactose, gum arabic, acrylates or methacrylates, cellulose acetyl phthalates, hydroxypropyl cellulose, hydroxypropyl methylcellulose, hydroxypropyl methylcellulosephthalate, hydroxymethylcellulose, polyvinyl pyrrolidone, shellac, bentonite, polyvinyl-acetatephthalate, phthalated gelatin, succinated gelatin, agar agar, hydroxyalkylstarches and mixtures thereof.

29. A solid dosage form obtainable according to the process of claim 14.

30. A solid pharmaceutical dosage form obtainable according to the process of claim 15.

31. A solid pharmaceutical dosage form according to claim 14, comprising a coating selected from the group consisting of cellacephate, polyvinyl acetate phthalate, methacrylic acid polymers, hypromellose phthalate, hydroxyalkyl methyl cellulose phthalates and mixtures thereof.

32. A solid dosage form according to claim 7, wherein the first and second capsule parts have the same or different lengths.

33. A solid dosage form according to claim 7, wherein the first and second capsule parts have the same or different colors.

34. A solid dosage form according to claim 7, wherein the solid dosage form is banded at the contact area of the capsule parts.

35. A solid dosage form according to claim 7, wherein the solid dosage form is easily dividable at the contact area of the capsule parts.

36. A solid dosage form according to claim 2, wherein the caplet contained in the capsule has a preformed step or groove so that the solid dosage form may be dividing into separate portions.

37. A dosage form according to claim 7, wherein the caplet contained in the capsule is uncoated or coated with an acceptable coating for tablet processing.

38. A process according to claim 1, wherein an adhesive is sprayed onto the surface of the caplet and/or onto the inner surface of the capsule parts immediately before assembling.

39. A process according to claim 38, wherein the adhesive is tackidex or an aqueous gelatin solution.

40. A solid dosage form according to claim 16 comprising a pharmaceutically active composition.

41. A solid dosage form according to claim 16 comprising an agrochemically active composition.

42. A solid dosage form according to claim 16 comprising a foodstuff composition.

43. A solid dosage form according to claim 16 comprising a dyestuff composition.

44. A solid dosage form according to claim 40, wherein the caplet contained in the capsule is a pharmaceutical composition with an active substance selected from the group consisting of betamethasone, thioctic acid, sotalol, salbutamol, norfenefrine, silymarin, dihydroergotamine, buflomedil, etofibrate, indomethacin, oxazepam, acetyldigitoxins, piroxicam, haloperidol, isosorbide mononitrate, amitriptyline, diclofenac, nifedipine, verapamil, pyritinol, nitrendipine, doxycycline, bromhexine, methylprednisolone, clonidine, fenofibrate, allopurinol, pirenzepine, levothyroxine, tamoxifen, metildigoxin, o-(B-hydroxyethyl)-rutoside, propicillin, aciclovirmononitrate, paracetamolol, naftidrofuryl, pentoxifylline, propafenone, acebutolol, 1-thyroxin, tramadol, bromocriptine, loperamide, ketofinen, fenoterol, ca-dobesilate, propranolol, minocycline, nicergoline, ambroxol, metoprolol, B-sitosterin, enalaprilhydrogenmaleate, bezafibrate, isosorbide dinitrate, gallopamil, xantinolnicotinate, digitoxin, flunitrazepam, bencyclane, despanthenol, pindolol, lorazepam, diltiazem, piracetam, phenoxymethylpenicillin, furosemide, bromazepam, flunarizine, erythromycin, metoclopramide, acemetacin, ranitidine, biperiden, metamizol, doxepin, dipotassiumchlorazepat, tetrazepam, estramustinephosphate, terbutaline, captopril, maprotiline, prazosin, atenolol, glibenclamid, cefaclor, etilefrin, cimetidine, theophylline, hydromorphone, ibuprofen, primidone, clobazam, oxaceprol, medroxyprogesterone, flecainide, Mg-pyridoxal-5-phosphateglutaminate, hymechromone, etofyllineclofibrate, vincamine, cinnarizine, diazepam, ketoprofen, flupentixol, molsidomine, glibornuride, dimethindene, melperone, soquinolol, dihydrocodeine, clomethiazole, clemastine, glisoxepid, kallidinogenase, oxyfedrine, baclofen, carboxymethylcystsin, thioredoxin, betahistine, 1-tryptophan, myrtol, bromelain, prenylamine, salazosulfapyridine, astemizole, sulpiride, benzerazid, dibenzepin, acetylsalicylic acid, miconazole, nystatin, ketoconazole, sodium picosulfate, colestyramate, gemfibrozil, rifampin, fluocortolone, mexiletine, amoxicillin, terfenadine, mucopolysaccharidpolysulfuric acid, triazolam, mianserin, tiaprofensaure, ameziniummethylsulfate, mefloquine, probucol, quinidine, carbamazepine, Mg-1-aspartate, penbutolol, piretanide, amitriptyline, caproteron, sodium valproinate, mebeverine, bisacodyl, 5-amino-salicyclic acid, dihydralazine, magaldrate, phenprocoumon, amantadine, naproxen, carteolol, famotidine, methyldopa, auranofine, estriol, nadolol, levomepromazine, doxorubicin, medofenoxat, azathioprine, flutamide, norfloxacin, fendiline, prajmaliumbitartrate, aescin acromycin, anipamil, benzocaine, B-carotene, cloramphenicol, chlorodiazepoxid, chlormadinoneacetate, chlorothiazide, cinnarizine, clonazepam, codeine, dexamethasone, dicumarol, digoxin, drotaverine, gramicidine, griseofulvin, hexobarbital hydrochlorothiazide, hydrocortisone, hydroflumethiazide, ketoprofen, lonetil, medazepam, mefruside, methandrostenolone, sulfaperine, nalidixic acid, nitrazepam, nitrofurantoin, estradiol, papaverine, phenacetin, phenobarbital, phenylbutazone, phenytoin, prednisone, reserpine, spironolactine, streptomycin, sulfamethizole, sulfamethazine, sulfamethoxoazole, sulfamethoxydiazinon, sulfathiazole, sulfisoxazole, testosterone, tolazamide, tolbutamide, trimethoprim, tyrothricin or mixtures thereof.

45. A solid dosage form according to claim 15, wherein the shell halves do not completely cover the caplet.

46. A solid dosage form according to claim 45, wherein each of the shell halves and the caplet have different colors.

47. A solid dosage form according to claim 46, wherein the shell halves have the same color and the caplet has a different color.

48. The process according to claim 13, wherein the moisture content is about 16 to about 18%.

49. The process according to claim 12, wherein the encapsulated dosage form is dried at a temperature in the range of from about 15 to about 60 C.

50. The process according to claim 49, wherein the encapsulated dosage form is dried at a temperature in the range of from about 18 to about 25 C.

\* \* \* \* \*